United States Patent
Day

[19]

[11] Patent Number: 5,829,978
[45] Date of Patent: Nov. 3, 1998

[54] SURFACE ROUGHENING OF SELF-TAPPING DENTAL IMPLANTS

[75] Inventor: Thomas H. Day, San Diego, Calif.

[73] Assignee: Sulzer Calcitek Inc., Carlsbad, Calif.

[21] Appl. No.: 966,817

[22] Filed: Nov. 10, 1997

[51] Int. Cl.⁶ ................................................ A61C 8/00
[52] U.S. Cl. .......................................... 433/174; 433/173
[58] Field of Search ................... 433/173, 174, 433/220, 221, 224, 225

[56] References Cited

U.S. PATENT DOCUMENTS

| | | | |
|---|---|---|---|
| 4,171,569 | 10/1979 | Rovins | 32/15 |
| 5,078,607 | 1/1992 | Niznick | 433/174 |
| 5,167,502 | 12/1992 | Kawahara et al. | 433/173 |
| 5,174,755 | 12/1992 | Fukuda | 433/173 |
| 5,188,800 | 2/1993 | Green, Jr. et al. | 422/23 |
| 5,209,659 | 5/1993 | Friedman et al. | 433/173 |
| 5,246,369 | 9/1993 | Poulmaire | 433/173 |
| 5,310,343 | 5/1994 | Hasegawa et al. | 433/173 |
| 5,324,199 | 6/1994 | Branemark | 433/174 |
| 5,338,197 | 8/1994 | Kwan | 433/174 |
| 5,344,457 | 9/1994 | Pilliar et al. | 623/16 |
| 5,417,569 | 5/1995 | Perisse | 433/173 |
| 5,503,558 | 4/1996 | Clokie | 433/173 |
| 5,571,017 | 11/1996 | Niznick | 433/174 |
| 5,588,838 | 12/1996 | Hansson et al. | 433/173 |
| 5,607,480 | 3/1997 | Beaty | 623/16 |

*Primary Examiner*—Nicholas D. Lucchesi
*Attorney, Agent, or Firm*—Philip S. Lyren

[57] ABSTRACT

A self-tapping dental implant includes a body which is substantially covered by random surface roughening without adversely affecting the cutting edge and thus the amount of torque needed to thread the implant into bone tissue. During the surface treatment process, the cutting edges of the implant are shielded from the roughening treatment.

17 Claims, 1 Drawing Sheet

SURFACE ROUGHENING OF SELF-TAPPING DENTAL IMPLANTS

BACKGROUND OF THE INVENTION

This invention relates generally to self-tapping dental implants and particularly to techniques for forming roughened surfaces on self-tapping dental implants.

Dental implants are used to provide a tooth-like structure in areas where both the tooth and the root are missing. Areas where all tooth structure is absent, called edentulous regions, may exist where one or more teeth have been lost.

A typical dental implant has a generally cylindrical structure. The cylindrical body of the implant is secured into the jawbone with the upper proximal edge or neck portion located at or above the jawbone crest. The neck portion often has a threaded bore for receiving an abutment that mounts the artificial tooth. The opposite end of the implant, called the distal end, is located in a position anchored within the jawbone.

By a process known as osseointegration, the implant becomes integrally bonded with the bone tissue over time. In this way the implant may be very securely retained in the jaw structure.

Self-tapping implants include at least one longitudinal cutting groove extending along the length of the implant body. Usually the cutting groove extends a substantial portion of the length of the implant down to its distal end. Two or more cutting grooves may be circumferentially spaced about the implant.

As the implant body is rotated into the bone structure, the cutting groove scrapes away bone tissue like a tap. These bone tissue fragments may be secured inside implant body openings adjacent the groove. Further, the bone fragments may re-grow to form bone that is interengaged with the implant.

Self-tapping dental implants have many advantages. One important advantage is that the implantologist is able to save time during the implantation process. Since the implant simultaneously taps the bone during insertion, a separate tapping stage is not necessary. This time saving results in economies as well as decreased air exposure to the exposed implantation site and, therefore, decreased likelihood of infection. In addition, self-tapping implants may have better stability and more intimate contact with the bone. Thus, self-tapping implants may achieve better osseointegration inter alia because of the bone fragments formed in the cutting process and the enhanced opportunity for the growth of new bone tissue.

Self-tapping implants should have relatively sharp cutting edges to avoid the necessity for very high insertion torque during installation. Greater insertion torque during insertion can damage the engaging neck portion at the proximal end of the implant. In addition, the need for high torque may result in an implant that is not fully seated in the bone tissue. Also, the need for high torque may increase the installation time.

Random surface roughness in dental implants, in general, increases the stability and osseointegration of those implants. One theory is that the roughened surface provides spacing between the implant and the bone surface where osseointegration may occur. While it is possible to machine roughened features onto the dental implant surface, random roughness may be more effective in achieving osseointegration.

One explanation for the integration that occurs due to surface roughening is that osteoblast-like cells cover the implant surface to integrate the bone. These cells are apparently able to attach themselves to the implant surface better when that surface is rough. Generally the micromorphologic characteristics of the surface determine the response of these cells to the implant.

Random surface roughness may result from either subtractive or additive processes. An example of a subtractive process is particle bombardment of the surface. Particle bombardment processes include grit blasting with titanium oxide or aluminum oxide. The amount of roughness achieved may be different depending on the particle size, force and duration. Another subtractive process is acid etching the surface, for example, using hydrofluoric acid. Similarly, ion etching, chemical milling, laser etching, and spark erosion may have applicability in dental implant surface roughening.

Additive processes may result in the build up of rough textured surface features on dental implants. Examples of additive processes include the molten titanium plasma spray or "TPS" process and the HA coating process. Generally, bone compatible bioreactive materials such as apatite materials can be used to form an HA coating on the implant surface. Examples of useful apatite materials include hydroxyapatite and whitlocktite.

The HA coatings may be high crystallinity, creating a roughness approximating that achieved with acid etching. Lower density or lower crystallinity HA coatings can match or exceed the roughness achieved through TPS or grit blasting.

The application of random surface roughening techniques to self-tapping implants raises an important issue. While surface roughening, like the self-tapping implant technology, aids in osseointegration, surface roughening, dulls the cutting edge or surface. In turn, this dulled edge increases the friction between the implant and the bone during installation. As a result, the necessary installation torque is increased, giving rise to the possibility of the problems attendant to increased torque, discussed above.

It would be very desirable to have a technique which enables self-tapping implants to be surface roughened without the need for increased insertion torques. Such techniques could enable the advantages of both the self-tapping technology and the random surface roughness technology to be achieved in a single implant.

Some self-tapping implants roughen a middle portion of the body and leave the entire distal end relatively unroughened. These implants maintain a sharp cutting edge. But, the benefits of roughening are not fully achieved on the implant body since a significant portion of the submerged implant is not roughened. An implant that had a roughened distal portion yet maintained a sharp cutting edge would be advantageous.

SUMMARY OF THE INVENTION

In accordance with one aspect of the present invention, a self-tapping dental implant includes a generally cylindrical body. At least one cutting edge extends over at least a portion of the body. The body includes a roughened surface region with the exception that the region of the cutting edge is substantially free of roughening. In certain embodiments, a plurality of cutting edges are spaced around the body of the implant.

In accordance with another aspect, a method for surface roughening is provided for a self-tapping dental implant that has cylindrical body with at least one cutting edge extending over the body. The method may include the step of exposing a substantial portion of the body to a roughening treatment. The cutting edge, however, is shielded from the treatment, and thus does not become dull. In certain embodiments, a spray may be directed at the implant to create a roughened surface, but the spray is prevented from contacting the cutting edge. In particular embodiments, the implant may be rotated while being subjected to a roughening spray. In still other situations, a shield may be interposed between the spray and the implant so as to protect a concave region on the implant. In some cases, abrasive particles may be sprayed and in some other cases, coatings may be sprayed.

One advantage of the present invention is the possibility of achieving the effects of surface roughening in self-tapping implants without the need for materially increased installation torque. In addition, in some instances, it may be possible to increase the potential area exposed to surface roughening without adverse effects on the cutting edge and hence on installation torque. Increased roughened surface area may also advantageously increase the force necessary to remove the implant once it is implanted.

The details of one or more embodiments of the invention are set forth in the accompanying drawings and the description below. Other features, objects and advantages will be apparent from the description and drawings, and from the claims.

DESCRIPTION OF THE PREFERRED EMBODIMENTS

Figure 1:
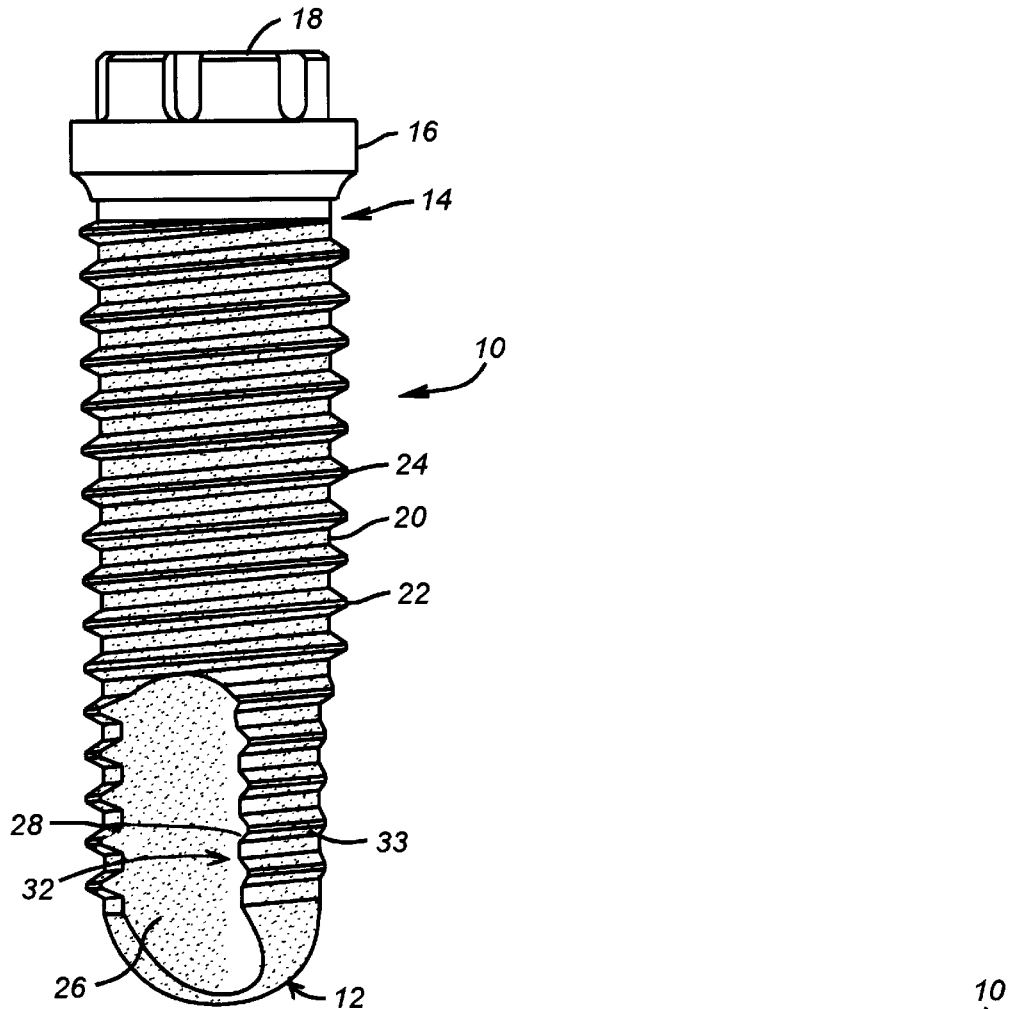
FIG. 1 is a front elevational view of one embodiment of the present invention.

Referring to the drawing wherein like reference characters are utilized for like parts throughout the several views, a self-tapping dental implant 10, shown in FIG. 1, includes a distal end 12 and a proximal end 14. Adjacent to the proximal end 14 is a neck portion 16 which may be unroughened. In one particular embodiment, the neck portion 16 includes an anti-rotational feature such as a plurality of splines 18 which prevent relative rotation with respect to an abutment, coping, or other prosthetic component (not shown) secured to the neck portion 16. Of course, the use of the anti-rotational feature is completely optional and other non-rotational structures known in the art may be used as well.

The body 20 of the implant 10 may be generally cylindrical with a slight proximal to distal taper. The distal end 12 may be slightly smaller in diameter than the portion of the body 20 adjacent the proximal end 14. The body 20 has a screw thread 22 formed on its surface. While the illustrated screw thread 22 includes a blunt edge 24, other configurations known in the art of the thread may be used as well.

The distal end 12 of the implant 10 includes one or more cutting edges or surfaces defining openings 26. The number of openings 26 may be varied, but commonly two or more openings 26 are used. The openings 26 may extend completely through the implant 10 or they may be formed as cavities defining depressions in the surface of the implant body. One exposed edge or surface along the opening 26 defines a longitudinal cutting edge 28. The cutting edge 28 scrapes bone fragments from the surrounding bone tissue as the gently tapering implant extends into the bone structure and rotation is applied to the neck portion 16. In the illustrated embodiment, with four openings 26, four cutting edges 28 extend longitudinally at approximately 90 degrees from one another.

A concave cutting surface 32 is defined in conjunction with each cutting edge 28. In addition, each cutting edge 28 is bounded on one side by a convex surface 33.

Substantially the entire surface of the body 20 is exposed to one or more random surface roughening treatments. The useful treatments include any known subtractive treatment, additive treatment, or other treatments known in the art (including those described above). In addition, as mentioned earlier, it is possible to follow a subtractive treatment with an additive treatment to achieve a desired degree of roughness. Generally, it is desirable to maximize the percentage of the body 20 in contact with bone tissue that is roughened. Maximizing the roughened area on the body aids osseointegration and increases the removal torque of the implant.

Referring to FIG. 1, a substantial portion of the surface of the body 20 is roughened while the concave surfaces including the cutting edges 28, are substantially unroughened. "Substantially unroughened" indicates that a region has not been exposed to the same extent of deliberate roughening processes as for example region 33. Preferably, the cutting edge 28 and neck portion have no roughening.

By eliminating the roughening about the cutting edges 28, the ability of the cutting edges 28 to cut the bone tissue is substantially unaffected by the roughening process. As a result, it is possible to use a self-tapping implant having the advantages of surface roughening without suffering the concommittant disadvantage of requiring increased installation torque.

Figure 2:
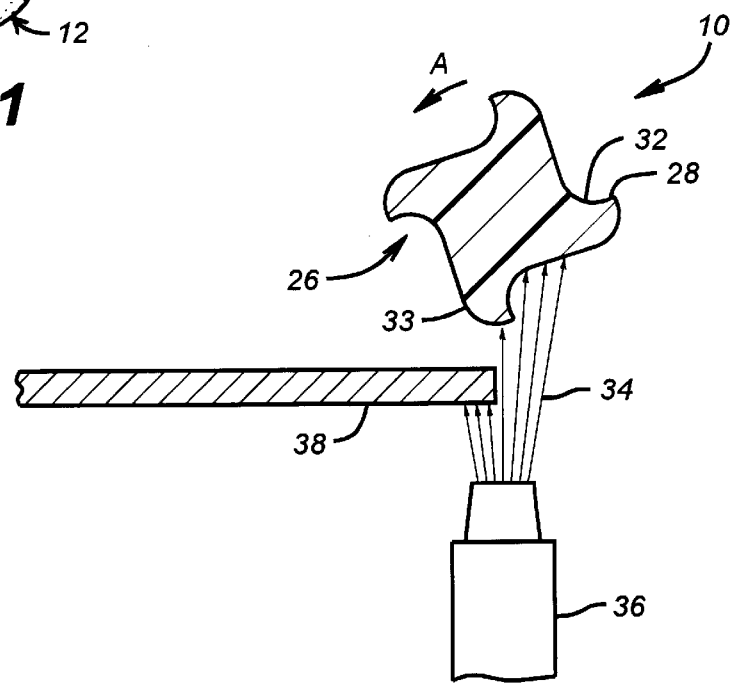
FIG. 2 is a partial cross-sectional view of the embodiment of FIG. 1 shown in the process of being exposed to a surface roughening treatment.

Referring to FIG. 2, the implant 10 is arranged with its length transverse to the direction of flow of a stream of roughening material 34 from an applicator 36. The applicator 36 may be a sprayer or other applicating device which ejects a spray of material 34 with sufficient force, in the case of abrasive material, to cause surface roughening of the implant 10. The stream 36 could also include additive roughening materials such as the materials necessary to form an HA coating, TPS or any other roughening coating. Likewise, the stream 34 could be in the form of ions, sparks or other forms of energy and/or particles.

A shield 38 is positioned to partially obstruct the flow of stream 34 and to protect the concave surfaces 32 and in particular the cutting edge 28. In fact, the positioning of the shield 38 may be varied to adjust the amount of exposure. In addition, the position of the shield 38 relative to the applicator 36 may be adjusted as well.

While the spray 34 is being directed against the implant 10, the implant 10 may be rotated in the direction of the arrow A in FIG. 2 so that the entire convex surface is eventually treated. Because of the concealed configuration of the concave surfaces 32 and the imposition of the shield 38, the cutting edges are substantially unaffected by the stream 34. However, substantially the entire region of the implant 10 other than the concave surfaces 32 are roughened as a result of their exposure to the stream 34.

Generally, the shield 38 should protect about half of the diameter of the implant 10 to prevent glancing blows from the stream 34 which could impact the cutting edges 28 before the cutting edges 28 are rotated out of position to be exposed to the stream 34.

The shielding arrangement can work even when the cutting edges 28 and the corresponding concave surfaces 32 are not linear. For example, if the shield 38 covers a substantial portion of the diameter of the implant 10. Even where the cutting edges 28 are spirally arranged about the implant 10, effective concealment of the cutting edges 28 can be achieved.

While the present invention has been described in connection with a limited number of preferred embodiments, those skilled in the art will appreciate numerous modifications and variations. It is intended that the appended claims cover all such modifications and variations as fall within the true spirit and scope of the appended claims.

What is claimed is:

1. A roughened self-tapping dental implant comprising:
   a body extending from a proximal end having a neck portion to a distal end having at least one cutting edge; and
   said body including a roughened surface region extending from said proximal end to said distal end, with the exception that the region of said neck portion and said cutting edge being substantially free of roughening.

2. The implant of claim 1 including a plurality of cutting edges extending longitudinally along said body, each of said cutting edges being spaced substantially equally from an adjacent cutting edge and being substantially free of roughening.

3. The implant of claim 1 including at least two cutting edges with a region between said two cutting edges, wherein said region is substantially roughened.

4. The implant of claim 1, wherein said roughening includes additive roughening.

5. The implant of claim 1, wherein said roughening includes subtractive roughening.

6. The implant of claim 1, wherein said roughening includes both subtractive and additive roughening.

7. A method for surface roughening a self-tapping dental implant having a body with at least one cutting edge extending over said body, said method comprising the steps of:

exposing a substantial portion of said body to a roughening treatment; and shielding the cutting edge on said body from said treatment.

8. The method of claim 7, including the step of exposing said body to a subtractive roughening treatment.

9. The method of claim 7, including the step of exposing said body to an additive roughening treatment.

10. The method of claim 7, including the step of exposing said body to both a subtractive and an additive roughening treatment.

11. The method of claim 7, including the step of shielding said cutting edge from all roughening treatments.

12. The method of claim 7 including the steps of directing a spray at said implant to create a roughened surface, and preventing said spray from contacting said cutting edge.

13. The method of claim 12 including the step of rotating said body while subjecting said body to a roughening treatment.

14. The method of claim 13 including the step of interposing a shield between said spray and said implant so as to protect said cutting edge on said implant from being exposed to said spray.

15. The method of claim 14 including the step of spraying abrasive particles at said implant.

16. The method of claim 14 including the step of spraying a coating material onto said implant.

17. The method of claim 12 wherein said implant has a concave surface associated with said cutting edge and a convex surface adjacent said concave surface, said method including the step of orienting said concave surface, said convex surface and said spray such that said concave surface is shielded from said spray and said convex surface is not shielded.

* * * * *